(12) United States Patent
Dieker et al.

(10) Patent No.: US 8,057,786 B2
(45) Date of Patent: Nov. 15, 2011

(54) COSMETIC AND DERMATOLOGICAL COMPOSITIONS IN PARTICULAR FOR THE TREATMENT OF KERATIN CONTAINING SUBSTRATES

(75) Inventors: Kurt Dieker, Rosengarten (DE); Jan Jänichen, Hamburg (DE); Wilfried Petersen, Hamburg (DE); Manuela Salmina-Petersen, Hamburg (DE); Michael Kinder, Hamburg (DE); Jessica Scholze, Hamburg (DE)

(73) Assignee: Dr. Straetmans Chemische Produkte GmbH, Hamburg (DE)

( * ) Notice: Subject to any disclaimer, the term of this patent is extended or adjusted under 35 U.S.C. 154(b) by 356 days.

(21) Appl. No.: 12/399,477

(22) Filed: Mar. 6, 2009

(65) Prior Publication Data
US 2009/0257972 A1    Oct. 15, 2009

(30) Foreign Application Priority Data

Apr. 14, 2008  (EP) .................................... 08154467

(51) Int. Cl.
*A61K 8/73* (2006.01)
*A61Q 5/00* (2006.01)
*A61Q 5/12* (2006.01)
*A61Q 19/00* (2006.01)

(52) U.S. Cl. ............... 424/70.13; 424/70.11; 424/70.28; 514/718; 514/777

(58) Field of Classification Search ............... 424/70.13, 424/70.11, 70.27; 514/781, 777, 20.7, 23, 514/54
See application file for complete search history.

(56) References Cited

U.S. PATENT DOCUMENTS

| 4,080,310 A | 3/1978 | Ng et al. ......................... 510/123 |
| 4,205,063 A | 5/1980 | Khalil et al. ................... 510/125 |
| 4,292,212 A | 9/1981 | Melby ........................... 510/121 |
| 4,676,978 A | 6/1987 | Cseh ............................. 510/121 |
| 4,786,494 A | 11/1988 | Hirota et al. .................. 510/119 |
| 4,803,071 A | 2/1989 | Iovine et al. ............... 424/70.13 |
| 5,288,484 A | 2/1994 | Tashjian .................... 424/70.13 |
| 5,482,704 A | 1/1996 | Sweger et al. ............. 424/70.13 |
| 5,776,476 A | 7/1998 | Billmers et al. .............. 424/401 |
| 2005/0188481 A1 | 9/2005 | Vona, Jr. ........................... 8/406 |
| 2005/0198747 A1 | 9/2005 | Emmerling et al. .............. 8/406 |
| 2005/0255067 A1 | 11/2005 | Leighton et al. ............. 424/70.2 |
| 2005/0287106 A1 | 12/2005 | Legendre ........................ 424/73 |
| 2006/0002880 A1 | 1/2006 | Peffly et al. ................ 424/70.13 |

FOREIGN PATENT DOCUMENTS

| EP | 0308190 | 3/1989 |
| EP | 0689829 | 1/1996 |
| EP | 0988023 | 3/2000 |
| EP | 1051967 | 11/2000 |
| EP | 1568351 | 8/2005 |
| EP | 1598046 | 11/2005 |
| JP | 2007176895 | 7/2007 |
| WO | WO 01/39721 | 6/2001 |

*Primary Examiner* — Gina C Yu
(74) *Attorney, Agent, or Firm* — Roberts & Roberts, LLP

(57) ABSTRACT

The present invention relates to cosmetic and/or dermatological compositions for the treatment of keratin containing substrates, comprising synergistic mixtures of modified starch polymers with defined molecular weights and cationic charges in a cosmetically acceptable medium. The synergistic mixtures of modified starches employed to manufacture compositions according to the present invention exhibit significant benefits over the existing modified starches employed according to the state-of-the-art in the treatment of keratin-containing substrates like human or animal hair, skin and nails. Another aspect of the present invention is the stabilization of the modified starch solutions used to manufacture the cosmetic and/or dermatological compositions according to the present invention against the growth of micro-organisms without traditional preservatives.

11 Claims, No Drawings

COSMETIC AND DERMATOLOGICAL COMPOSITIONS IN PARTICULAR FOR THE TREATMENT OF KERATIN CONTAINING SUBSTRATES

The present invention relates to cosmetic and/or dermatological compositions in particular for the treatment of keratin containing substrates, comprising synergistic mixtures of modified starch polymers with defined molecular weights and cationic charges in a cosmetically acceptable medium.

The synergistic mixtures of modified starches employed to manufacture compositions according to the present invention are believed to exhibit significant benefits over the existing modified starches employed according to the state-of-the-art in the treatment of keratin-containing substrates like human or animal hair, skin and nails.

Another aspect of the present invention is the stabilization of the modified starch solutions used to manufacture the cosmetic and/or dermatological compositions according to the present invention against the growth of micro-organisms without traditional preservatives.

BACKGROUND OF THE INVENTION

Hair is composed of keratin, a cystein-rich fibrous protein. The high amount of acidic sulfhydryl-groups in the protein consequently leads to a net anionic charge of the hair cuticle under the pH-conditions of a regular shampoo. This anionic charge of the hair opens perspectives for a surface treatment with cationic polymers with the goal to improve the physical properties of the hair. Such cationic polymers have the ability to form adherent films on the anionic surface of the hair cuticle. This surface treatment of the hair is known as conditioning. Hence, cationic polymers are widely used as conditioners to facilitate wet and dry hair combing, to suppress static charging or to facilitate the detangling of the hair.

The demands to suitable cationic polymers are diverse. They have to exhibit an immediate effect in order to be judged positively by the applicant and their properties have to be balanced carefully in order to provide the desired effects for the specific application without exhibiting undesired side-effects. For example, on one hand they have to exhibit a sufficient adhesion to the hair in order to prevent removal during the rinsing process of the hair, on the other hand they should not form multilayer films with subsequent overload. Furthermore, they have to be compatible to aqueous systems in order to enable the production of suitable cosmetic formulations but at the same time the films shall have an intrinsic resistance towards the uptake of humidity on the hair.

The two characteristics of a cationic polymer which mainly determine the character of the films are the molecular weight and its level of cationic charge. Depending on the hair type and the desired applications those two characteristics have to be adjusted carefully in order to obtain the desired conditioning effects.

As the skin also provides a slightly acidic surface, similar considerations can also be applied to topical applications. In these applications it is known that cationic polymers can form adherent films on the skin, thereby promoting effects like softness. In cases where the film reduces the trans-epidermal water loss, cationic polymers can improve moisture retention and skin humidity.

As for the hair, the film forming properties of suitable cationic polymers have to be adjusted finely in order to exploit the full potential of skin conditioning without overload of the surface.

The cationic conditioners currently employed in formulations for the treatment of keratin-containing substrates are based on different polymeric backbones. They mainly consist of cationic polymers, proteins or protein derivatives or fatty quaternary ammonium compounds. Commonly used cationic polymers include quaternary nitrogen-containing hydroxyethyl cellulose compounds, copolymers of vinylpyrrolidone and dimethylamino-ethylmethacrylate, and amino functional polydimethyl-siloxane. Hydrolyzed animal protein has been frequently used as a keratin conditioner. Also used are natural products such as collagen and casein.

The beneficial properties of co-polymers based on dimethyl diallylammonium chloride and acrylamide have been employed in toilet bars (EP 0,308,189), the use of hydroxyethyl cellulose cross linked with dimethyl diallylammonium chloride has been described in EP 0,308,190 and U.S. Pat. No. 4,803,071.

While these polymers provided acceptable solutions with respect to handling and cosmetic performance they exhibit the disadvantage of a poor biodegradability with the consequence of accumulation in the environment.

As a consequence of the growing environmental awareness, polymers based on natural backbones have been developed in order to provide an improved inherent biodegradability. These natural backbones initially were found in the class of polysaccharides such as cellulose and polypeptides such as guar.

Hair care compositions comprising cationic cellulose are well known. For example hydroxypropyl trimethyl ammonium chloride ethers of cellulose, widely known as Polyquaternium-10, have been used in conditioning or shampoo compositions (see U.S. Pat. No. 5,288,484, respectively U.S. Pat. No. 4,205,063) and can be considered state-of-the art treatments for keratinous substrates. Due to its strong interaction with the hair cuticle Polyquaternium-10 very well improves the combing properties on the hair. On the other side it tends to accumulate on the hair reducing its manageability.

Cationically modified guar gums such as hydroxypropyl trimethyl ammonium chloride ethers of guar have also been used extensively in hair care compositions. While their conditioning capacity is limited, quaternized Guar Gums contribute to a creamy and cosmetic perception of cosmetic products containing this cationic species. U.S. Pat. No. 4,292,212 therefore describes the use of this material in a shampoo crème rinse while U.S. Pat. No. 4,676,978 describes the use of this material in a shampoo.

As the quaternization of natural polymers reduced their biodegradability, non-ionic cellulose materials have been developed and can also be found in hair care formulations. E.g. U.S. Pat. No. 4,786,494 describes shampoo compositions which comprise a non-ionic cellulose ether compound and a hair conditioning composition comprising hydroxyethyl cellulose.

In the past years liquid modified starch materials have been developed in order to find a remedy for the handling disadvantages powder state conditioners. E.g. EP 1,051,967 describes cosmetic compositions containing oxidatively degraded modified starches and methods of stabilizing liquid formulations of these modified starches by addition of urea and/or α-hydroxy acids. Another application claims comparable liquid formulations of modified starches and their use in the treatment of keratinous substrates (see WO 0,139,721).

While the liquid and stable formulations available by these technologies provide the benefit of easy handling in production scale applications, the cosmetic formulations based on the claimed liquid starch solutions, however, have the disadvantages that in many cases they are of lower performance than comparable cosmetic formulations with other state-of-the-art modified polymers. Especially the immediate performance of the current cationic starch conditioners is insufficient in comparison to Polyquaternium-10 and therefore the evaluation of the applicant is not in favour of products containing these conditioners. In addition the stabilized liquid starch solutions are prone to microbiological deterioration and require preservative stabilization (see WO 0,139,721).

Various modifications of starch polymers and cosmetic compositions containing these starch derivatives have been developed in the past years for specific applications or to find a remedy to the low conditioning performance of the marketed cationic starch conditioners.

EP 0,988,023 discloses skin care compositions containing hydrophobic starch modified with calcium salts of dicarboxylic acids. These modified starches are described to improve the aesthetic appearance of the formulation.

Cosmetic compositions containing amphoteric aminomulticarboxylate modified starch is disclosed for modifying the rheological properties of cosmetic compositions in EP 0,689,829 and U.S. Pat. No. 4,080,310 discloses the use of a cationic starch in an amphoteric conditioning shampoo.

EP 1,598,046 describes mixtures of natural and synthetic polymers to form fixative films. As natural polymer chemically modified starches are claimed in combinations with e.g. Polyquaternium-4.

A method and composition to achieve stable colour of artificially coloured hair employing amylase containing starch is described in EP 1,568,351 and US 2005/0287,106 describes the use of modified starches to improved the efficacy of shaving formulations.

A further attempt to eliminate disadvantages of cationic starch polymers is described in US 2006/002,880. In this application, cosmetic formulations containing combinations of low molecular weight quaternized starches with co-acervates have been described. According to this patent application polyethoxylated anionic surfactants serve as co-acervates and the molecular weight of the quaternized starch polymer is <200.000 Da. This application addresses the topic of improved conditioning properties of skin and hair and describes the use of starch polymers of different sizes and degree of quaternization. However, it does not investigate into mixtures of modified starch polymers. Further, it has been found that the claimed formation of co-acervates can lead to the formation of turbidity and can therefore be contraindicated for the formulation of transparent formulations.

Therefore there remains a need for a cosmetic and/or dermatological composition which is in particular suitable for the treatment of keratinous substrates such as hair, animal hair, skin or nails which:
a) meets or exceeds the conditioning performance of state-of-the-art formulations, characterized by the immediate wet and dry combing performance, the static charging of the hair and the detangling performance
b) is flexible towards the specific demands of different types of keratinous substrates
c) can be manufactured easily with stable liquid formulations of inherently biologically degradable polymers
d) can be removed easily from the keratinous surface in order to avoid accumulation and consequently a poor manageability of the hair.

In addition, a growing demand for cosmetic formulations which do not contain traditional preserving agents exists. As many raw materials with conditioning properties and especially their aqueous systems are prone to microbiological contaminations they contain traditional preservatives for the in-can stabilization. Hence, the formulation of preservative-free systems is difficult according to the state-of-the-art.

Surprisingly, it has been found that the liquid modified starch polymers employed in compositions according to the present invention can be stabilized against microbiological contamination and therefore exhibit excellent solutions to deficiencies of the state-of-the-art.

SUMMARY OF THE INVENTION

The present invention comprises cosmetic and/or dermatological compositions. These compositions contain synergistic mixtures of water-soluble modified starches of defined molecular weight and cationic charge.

Cosmetic and/or dermatological compositions for the treatment of keratin containing substrates according to the present invention comprise as conditioner
a) between 0.01-10.0 wt. % of a linear or branched modified starch polymer of the general formula

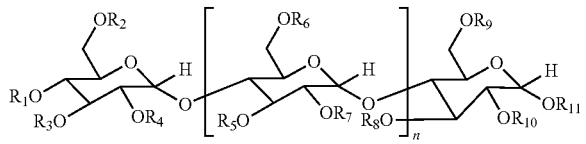

where $R_1$ to $R_{11}$ are independently H or a hydroxyalkyl residue of the general formula $-CH_2-CHOH-R_{12}$ with $R_{12}$ being $-CH_3$ or $-CH_2NR_{13}(CH_3)_2{}^+X^-$ with $R_{13}=-CH_3$ or a linear or branched $C_4$-$C_{22}$-alkyl residue and with $X^-=Cl^-$, $Br^-$ or $I^-$, where n is such that the average molecular weight of the polymer (I) is in the range of 200,000-1,000,000 Da and where the amount of hydroxyl groups carrying a cationic charge is between 25 wt. % and 50 wt. %, which corresponds to a degree of quaternization of D.S.=0.75 and 1.50 and
b) between 0.01 and 10.0 wt. % of a linear or branched modified starch polymer of the general formula

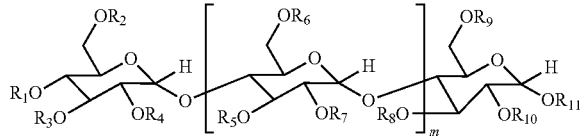

where $R_1$ to $R_{11}$ are independently H or a hydroxyalkyl residue of the general formula $-CH_2-CHOH-R_{12}$ with $R_{12}$ being $-CH_3$ or $-CH_2NR_{13}(CH_3)_2{}^+X^-$ with $R_{13}=-CH_3$ or a linear or branched $C_4$-$C_{22}$-alkyl residue and with $X^-=Cl^-$, $Br^-$ or $I^-$, where m is such that the average molecular weight of the polymer (II) is in the range of 2,000,000-8,000,000 Da and where the amount of hydroxyl groups carrying a cationic charge is between 2 wt. % and 20 wt. %, which corresponds to a degree of quaternization of D.S.=0.06 and 0.60 in a cosmetic acceptable medium.

The formulations according to the present invention containing synergistically acting modified starches can be obtained either by addition of mixtures of the liquid modified starches according to a) and b) or in the form of the isolated liquid solutions of a) and b) during the manufacturing process of the cosmetic formulation. In addition, the water based modified starch systems a) and/or b) employed to manufacture cosmetic and/or dermatological compositions according to this invention do not require traditional preservatives as defined by the European cosmetic directive 76/768/EC e.g. parabens and therefore allow the formulator to formulate the respective compositions without the use of traditional preserving systems.

A preferred use of the cosmetic and/or dermatological compositions according to the invention is for the treatment of keratin containing substrates, such as human or animal hair, skin or nails.

DETAILED DESCRIPTION OF THE INVENTION

According to the state of the art, quaternized starch polymers employed to produce formulations for the treatment of keratinous substrates can be obtained from different vegetable sources such as wheat, oat, barley, potato, corn, rice or cassava. In the first step of the manufacturing process of these modified polymers, the starch is normally degraded by chemical treatments such as acid hydrolysis or oxidation. The molecular weight distribution of the resulting degraded starch can be controlled by the conditions of the process. Subsequently, the degraded starch polymer can be alternatively quaternized directly or it can be previously modified to form non-ionic system and subsequently be quaternized. The degree of quaternization depends on the quantity of quaternization agent used in the subsequent modification step.

The quaternized starch polymers obtained by this state-of-the art manufacturing processes are characterized by more or less defined molecular weight distributions and degrees of quaternization.

The standard method to determine the molecular weight distribution of polymers is the gel permeation chromatography (GPC) coupled with multi angle laser light scattering (MALLS). Investigations of the modified starch polymers obtained by these techniques revealed that the molecular size of the polymers roughly follows a statistical curve with a more or less defined maximum. The same can be assumed for the degree of quaternization.

Stable liquid formulations of these quaternized starches can be obtained in concentrations up to approx. 25 wt. % with additives such as α-hydroxy acids and/or urea. In addition these commercially available liquid formulations of quaternized starches need to be preserved with traditional preserving systems. In formulations for the treatment of keratinous substrates the so obtained quaternized starch solution are recommended to be used in concentrations between 1.0-6.0 wt. %.

Investigations of market products by the above mentioned method revealed that the majority of quaternized starch derivatives employed in formulations for the treatment of hair and skin contain polymers of average molecular weights varying between 200,000 and 6,000,000 Da and quaternization grades between 5 wt. % and 50 wt. %.

In contrast to commercially available quaternized starch solutions, the stabilization of quaternized starches against microbiological deterioration according to the present invention can be optionally achieved by addition of organic acids from the group of masking agents or fragrances e.g. levulinic acid and/or p-anisic acid, polyols from the group of monoglycerides of fatty acids with 8-12 carbons e.g. Glyceryl Caprylate or 1,2-diols with 5-10 carbons e.g. Caprylyl Glycol and/or surfactants from the group of lactylates of fatty acids with 8-12 carbons, e.g. Sodium Lauroyl Lactylate.

Without limiting the present invention to a defined manufacturing method, the quaternized starch polymers used in cosmetic formulations according to this invention are manufactured by a) chemical degradation of starch b) if applicable non-ionic modification (e.g. hydroxyalkylation) of the degraded polymer c) quaternization of the resulting polymer and d) addition of stabilizing additives such as □-hydroxy acids, urea and optionally e) levulinic acid, p-anisic acid, polyols from the group of monoglycerides of fatty acids with 8-12 carbons or 1,2-diols with 5-10 carbons and/or surfactants from the group of lactylates of fatty acids with 8-12 carbons.

The performance of hair care formulations containing available modified starch polymers has been studied depending on the molecular size distribution and the degree of quaternization. The following test shampoo has been employed to evaluate the conditioning performance of the single products. The conditioners were added as 1 wt. % of the active substance in aqueous solutions.

| Test Shampoo | | | |
|---|---|---|---|
| Ingredient | INCI | Supplier | Conc. (%) |
| Tap Water | Aqua | | 47.10 |
| Dermofeel ® PA-3 | Sodium Phytate | Dr. Straetmans | 0.10 |
| Texapon N70 (70% AS*) | Sodium Laureth Sulfate | Cognis | 14.00 |
| Amphotensid B 5 (40% AS unpreserved) | Cocoamidopropyl Betaine | Zschimmer& Schwarz | 10.00 |
| Setacin 103 Spezial (40% AS) | Disodium Laureth Sulfosuccinate | Zschimmer& Schwarz | 5.00 |
| Dermosoft ® 1388 | Glycerin, Parfum, Aqua | Dr. Straetmans | 3.00 |
| Citric Acid (sol. 20%) | Citric Acid | | q.s. |
| Parf. Leafs in the trees | Parfum | Symrise | 0.80 |
| Conditioner (1% AS) | See table 1 | | 20.00 |
| | | | 100.00 |

AS = active substance

The following Table 1 shows comparative data of the relative wet combing forces after one and after five shampoo washings with shampoos containing different conditioning systems.

TABLE 1

Wet combing forces of commercially available quaternized starch polymers after one and five shampoo applications. All values are average values of three combing experiments.

| | Shampoo without Conditioner | | Shampoo + 0.2 wt. % AS Amylomer 25 L | | Shampoo + 0.2 wt. % AS Amylomer 100 S | | Shampoo + 0.2 wt. % AS Sensomer CI 50 | | Shampoo + 0.2 wt. % AS PQ 10 | |
|---|---|---|---|---|---|---|---|---|---|---|
| | abs. (g) | rel. wt. % | abs. (g) | rel. wt. % | abs. (g) | rel. wt. % | abs. (g) | rel. wt. % | abs. (g) | rel. wt. % |
| Initial wet combing force | 36.8 | 100 | 61.4 | 100 | 63.1 | 100 | 70.7 | 100 | 101.7 | 100 |
| 1 × Shampoo | 58.9 | 160 | 69.0 | 112 | 47.1 | 75 | 58.4 | 82 | 64.4 | 63 |
| 5 × Shampoo | 193.8 | 527 | 45.2 | 73 | 51.5 | 82 | 36.1 | 51 | 35.9 | 35 |

TABLE 2

Average molecular weights and quaternization of commercially available quaternized starch polymers (determined by GPC-MALLS)

| Product | Average mol weight | Average degree of quaternization |
|---|---|---|
| Amylomer ® 25 L | $4.8 \times 10^6$ g/mol | ~8% |
| Amylomer ® 100 S | $2.7 \times 10^5$ g/mol | ~33% |
| Sensomer ® CI 50 | $2.0 \times 10^6$ g/mol | ~17% |

It can be summarized from these investigations, that neither quaternized starch polymers of high molecular weight and low degree of quaternization (Amylomer® 25 L) nor polymers of relatively low molecular weight and high degree of quaternization (Amylomer® 100 S) exhibited substantial improvement of hair combability. Medium size polymers with a medium degree of quaternization (Sensomer® CI 50) which consequently have been developed to balance out these properties exhibit a satisfying reduction of combing force after several applications, however their instant efficacy is rather poor in comparison to the benchmark Polyquaternium-10.

In addition, the judgement of the tactile properties of the treated hair revealed that polymers of high average molecular weight form rather soft films on hair and skin which tend to be sticky. In contrary, if the molecular weight is too low and the quaternization too high, the resulting films have shown to be stiff. Regarding the quaternization it was found that if the degree of quaternization is too high the resistance towards humidity is low and multilayer-films (build-up) can be formed. If the degree of quaternization is too low the adhesion to the anionic surface suffers.

In conclusion of these initial investigations we found that the modified starch polymers in the form they are obtained in the previously described manufacturing process are not capable to balance out the inherent contradictory tendencies of the system. Hence, they are not able to provide acceptable conditioning solutions for hair and skin care formulations and to comply with the complex demands of a good and fast acting conditioner.

Unexpectedly, the inventors now have discovered that hair care formulations containing mixtures of:
a) quaternized starch polymers with a high molecular weight and a low degree of quaternization and
b) quaternized starch polymers with a low molecular weight and a high degree of quaternization
are capable to overcome these deficiencies of the state-of-the-art.

Cosmetic and/or dermatological compositions for the treatment of keratin containing substrates according to the present invention therefore comprise as conditioners
a) between 0.01-10.0 wt. % of a linear or branched modified starch polymer of the general formula

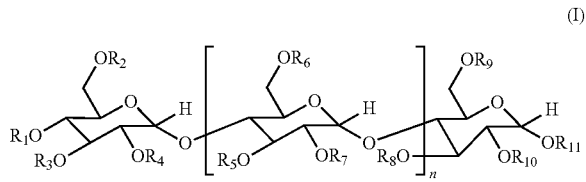

(I)

where $R_1$ to $R_{11}$ are independently H or a hydroxyalkyl residue of the general formula —$CH_2$—CHOH—$R_{12}$ with $R_{12}$ being —$CH_3$ or —$CH_2NR_{13}(CH_3)_2{}^+X^-$ with R13=—$CH_3$ or a linear or branched $C_4$-$C_{22}$-alkyl residue and with $X^-$=$Cl^-$, $Br^-$ or $I^-$, where n is such that the average molecular weight of the polymer (I) is in the range of 200,000-1,000,000 Da and where the amount of hydroxyl groups carrying a cationic charge is between 25 wt. % and 50 wt. %, which corresponds to a degree of quaternization of D.S.=0.75 and 1.50 and
b) between 0.01 and 10.0 wt. % of a linear or branched modified starch polymer of the general formula

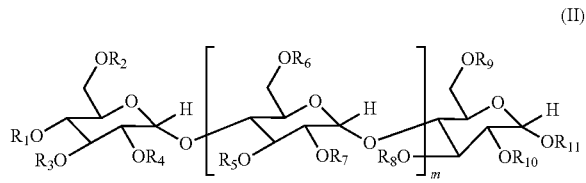

(II)

where $R_1$ to $R_{11}$ are independently H or a hydroxyalkyl residue of the general formula —$CH_2$—CHOH—$R_{12}$ with $R_{12}$ being —$CH_3$ or —$CH_2NR_{13}(CH_3)_2{}^+X^-$ with $R_{13}=$—$CH_3$ or a linear or branched $C_4$-$C_{22}$-alkyl residue and with $X^-=Cl^-$, $Br^-$ or $I^-$, where m is such that the average molecular weight of the polymer (II) is in the range of 2,000,000-6,000,000 Da and where the amount of hydroxyl groups carrying a cationic charge is between 2 wt. % and 20 wt. %, which corresponds to a degree of quaternization of D.S.=0.06 and 0.60
in a cosmetic acceptable medium.

TABLE 3

Wet combing forces of different combinations of Amylomer 25 L and Amylomer 100 S after one and five shampoo applications. All values are average values of three combing experiments.

|  | Shampoo without Conditioner | | Shampoo + 0.13 wt. % Amylomer 25 L + 0.07% Amylomer 100 S | | Shampoo + 0.1 wt. % Amylomer 25 L + 0.1% Amylomer 100 S | | Shampoo + 0.07 wt. % Amylomer 25 L + 0.13% Amylomer 100 S | | Shampoo + 0.2% PQ 10 | |
|---|---|---|---|---|---|---|---|---|---|---|
|  | abs. (g) | rel. wt. % | abs. (g) | rel. wt. % | abs. (g) | rel. wt. % | abs. (g) | rel. wt. % | abs. (g) | rel. wt. % |
| Initial wet combing force | 36.8 | 100 | 47.8 | 100 | 51.3 | 100 | 57.5 | 100 | 101.7 | 100 |
| 1 × Shampoo | 58.9 | 160 | 22.9 | 48 | 22.5 | 44 | 20.8 | 36 | 64.4 | 63 |
| 5 × Shampoo | 193.8 | 527 | 26.9 | 54 | 28.1 | 55 | 18.9 | 33 | 35.9 | 35 |

As shown in table 3, formulations containing mixtures of different quaternized starch polymers according to the present invention not only exhibited superior conditioning efficacy in comparison to compositions containing existing quaternized starch polymers they also exhibited superior initial conditioning efficacy in comparison to the market standard Polyquaternium-10.

In addition, Rubin Dye tests of treated hair swatches have revealed that even though the intensity of the conditioning layer of the quaternized starch polymers according to the present invention was comparable to the layer of Polyquaternium-10, it could be removed much easier from the surface of the hair than the conditioning layer of the latter on. As a consequence the risk of accumulation of conditioner on the hair cuticle is remarkably reduced in formulations according to the present invention.

It can be assumed from these findings that the effect of the synergistic mixtures of quaternized starch polymers can be explained by a two layer model. The polymers of low molecular weight and high degree of quaternization have the capacity to interact strongly with the surface of the cuticle and to fill easily the holes of damaged hair. The high molecular weight polymers with lower degree of quaternization build a second layer which covers the cuticle homogenously.

Also skin care formulations containing combinations of modified starch polymers have been studied. In an elbow washing test a panel of 17 persons tested two shower gel formulations, one containing 0.2 wt. % active of a 2:1 mixture of Amylomer 100 S and Amylomer 25 L against placebo.

It has been found that the test shower gel containing combinations of modified starch polymers was judged superior against the placebo formulation with respect to skin roughness (82 wt. %) and mildness (76 wt. %) by the test person. Further the higher creaminess of the formulation containing synergistic combinations of modified starch polymers during the application was noticed by 65 wt. % of the test panel.

Formulation of the Modified Starch Polymers:

The cosmetic and/or dermatological formulations for the treatment of keratin containing substrates employing mixtures of defined modified starch polymers can be considered novel as they have not been described before and are not inherently available by adding quaternized starch polymers which have been manufactured by standard quaternization processes. The defined quaternized starch polymers have to be manufactured in isolated manufacturing processes. The fact that these quaternized starch polymers in contrast to commercially available starch derivatives are stabilized without traditional preserving systems can be considered novel as well.

The formulations according to the present invention can be easily prepared by a person skilled in the art by addition of the aqueous solutions of the defined modified starch polymers to a cosmetic formulation under consideration of potential incompatibilities. More convenient, however, is the use of aqueous based blends of different modified starch polymers which are explicitly included in this patent.

The cosmetic and/or dermatological formulations of the present invention can be employed in different product applications for the treatment of keratin containing substrates.

a) Hair Treatment

For the treatment of hair, the mixtures of quaternized starch polymers can be employed e.g. in shampoos for the different hair types, conditioners, hair fixatives or relaxers, hair toners, colours or bleaches, hair gels, foams or waxes. Such formulations can be manufactured easily by persons skilled of the art. The cosmetically acceptable medium is selected according to the intended application and based on the compatibility of its ingredients. In addition to the cationic starch polymers the compositions of the present invention can further comprise additional conditioners, surfactants, thickeners, pearlescents, fragrances, oils, viscosity regulators, dyes, foam boosters, propellants or actives such as anti-dandruff actives.

Additional conditioners may be added to the formulation and may result in additional synergistic effects. These conditioners may be selected from the group of cationic polyhydroxyl compounds, silicon oils or silicone derivatives, cationic surfactants or cationic polymers or mixtures thereof. Non-limiting examples of cationic polyhydroxyl compounds are polyquaternium-10 or guar hydroxypropyl trimonium chloride. From the group of silicon oils dimethicone or cyclomethicone may be selected from the group of silicone derivates quaternium-80 may be chosen. Cationic surfactants may precipitate in complex with anionic surfactants during the rinsing process and may provide additional conditioning effect. From the group of cationic surfactants cetrimonium chloride, stearalkonium chloride or palmitamidopropyl trimonium chloride may be used. Other conditioning agents may be useful in formulations according to the present invention such as polyquaternium-4, polyquaternium-7, polyquaternium-11, polyquaternium-22, polyquaternium-39 or mixtures thereof.

Surfactants can be chosen from the group of anionic, amphoteric or non-ionic surfactants. Specific non-limiting examples from the group of anionic surfactants are alkyl sulfates e.g. alkali lauryl sulfates, alkyl ether sulfates e.g. alkali laureth sulfate alkyl or acyl sarcosinate e.g. sodium lauroyl sarcosinate, sulfosuccinates such as disodium N-octadecylsulfosuccinnate or disodium lauryl sulfosuccinate, diammonium lauryl sulfosuccinate, tetrasodium N-(1,2-dicarboxyethyl)-N-octadecylsulfosuccinnate, diamyl ester of sodium sulfosuccinic acid, dihexyl ester of sodium sulfosuccinic acid, and dioctyl esters of sodium sulfosuccinic acid, acylisethionates e.g. sodium cocoyl isethionate and combinations thereof. Amphoteric surfactants are in general components which contain a quaternized ammonium group and a carboxylate or sulfonate group in the same molecule. Specific non-limiting examples from the group of amphoteric surfactants are alkylamidobetaines e.g. cocoamidopropyl betaine, alkylamphoacetates e.g. sodium cocoamphoacetate or disodium cocoamphoacetate Non-ionic surfactants may be chosen from the group of polyglyceryl esters e.g. polyglycerin-10 laurate, sorbitanester or alkylpolyglucosides e.g. coco glucoside or may be products which result from an addition reaction of ethylene or propylene oxide to fatty alcohols, fatty acids, alkyl phenols or ricinoleic acid, sorbitan esters or glycerides e.g. PEG-40 hydrogenated castor oil, Polysorbate 20.

Suitable consistency agents can be chosen from the group of fatty alcohols or hydroxyl fatty alcohols with 12 to 22 carbons, partial glycerides, fatty acids or hydroxy fatty acids. Thickeners can be chosen from the group of polysccharides such as xanthan gum, guar, agar, alginates or tyloses, carboxymethylcellulose or hydroxyethyl- and hydroxypropylcellulose. Also polyacrylates from the Carbopol or Pemulene types are suitable thickeners as well as polyacrylamides, polyvinyl alcohols or PVP or mixtures of these systems can serve as thickeners according to the present invention.

Suitable opacifying systems include, for example alone or in mixture alkylene glycolester, especially ethylenglycol distearate, fatty acid alkanolamides, especially cocofatty acid diethanolamide; partial glycerides, such as glyceryl monostearate; ester of polyalcohols, if applicable hydroxy-substituted carboylic acids with fatty alcohols with 6 to 22 carbon atoms, especially of higher alcohols and tartaric acid; fatty alcohols, fatty ketones, fatty aldehydes, fatty ethers or fatty carbonates which contain at least 24 carbon atomes, especially distearyl ether; fatty acids like stearic acid, hydroxystearic acid, or behenic acid, ring opening products from olefin epoxides with 12 to 22 carbon atoms and fatty alcohols with 12-22 carbon atoms or polyols with at least 2-15 carbon atoms and 2 to 10 hydroxyl groups.

Suitable oils may be added to the formulation and can further improve the conditioning efficacy. These oils can be selected from the group silicone oils, hydrocarbon oils, polyolefins, triglycerides, and fatty esters, ethers or carbonates or combinations thereof.

Dyes may be added to the formulation in order to obtain hair toners or colorants. These dyes may be selected from the group of permanent or oxidation dyes, semi-permanent dyes or temporary dyes.

Suitable propellants have a vapour pressure at 1 atm of less than about 21° C. Non-limiting examples of suitable propellants are alkanes, isoalkanes, haloalkanes, dimethyl ether, nitrogen, nitrous oxide, carbon dioxide, and mixtures thereof.

Suitable non-limiting examples of anti-dandruff actives include pyridinethione salts, azoles, selenium sulfide, particulate sulphur, keratolytic agents, and mixtures thereof. Such anti-dandruff actives should be physically and chemically compatible with the essential components of the composition, and should not otherwise unduly impair product stability, aesthetics or performance.

Preserving agents: The quaternized starch polymers employed according to the present invention do not contain preservatives as defined in the annex VI of the European cosmetic directive 76/768/EC. Therefore formulations without said preservatives may be realized. Nevertheless, the formulator may also add preservatives according to the annex VI of the European cosmetic directive 76/768/EC in order to enhance the stability against microbial deterioration. Non-limiting examples of system which may be used are esters of p-hydroxybenzoic acid, phenoxyethanol, sorbic acid, benzoic acid, methylisothiazolinone, formaldehyde or doners of formaldehyde such as DMDM-hydantoin or imidazolidinyl urea.

Method of Manufacturing:

The defined mixtures of the cationic starch polymers can be introduced into manufacturing process of the cosmetic product either as blends or separately. Preferably, they should be added to the aqueous phase containing the surfactant system. The addition of the cationic starch polymers may be executed at any temperature between room temperature or 80° C. Heat sensitive or volatile ingredients should be added to the formulation at the end at room temperature.

b) Skin Treatment:

For the treatment of skin, mixtures of quaternized starch polymers can be employed in products such as shower gels, soaps, creams, lotions, gels, products for sun protection or after sun treatment or in decorative cosmetics such as mascara, eye shadow, lip sticks or powders. Such formulations can be manufactured easily by persons skilled of the art and can further comprise surfactants, emulsifiers, oils, moisturizers, thickeners and viscosity regulators, pigments, UV-filters, antioxidants, solubilizers, refattying agents or actives.

Surfactants may be chosen from the same group mentioned above for the hair treatment products.

Emulsifiers may be chosen from the group of non-ionic or anionic emulsifiers. Non-ionic emulsifiers can be esters of fatty acid with chain length between 8 and 22 carbons and glycerine or polyglycerin with a degree of polymerization between 2 and 10. Also suitable are ethers or esters of mono- or polysaccharides and products resulting from an addition process of ethylene oxide or propylene oxide to fatty acids, fatty alcohols, glycerides or saccharides. Anionic emulsifiers may be chosen from the group alkali acyl lactylates, e.g. sodium stearoyl lactylate, esters of citric acid or tartric acid with glycerides e.g. glyceryl stearate citrate or alkyl phosphates. All emulsifiers may be used alone in as mixtures.

Products for the treatment of skin, like creams, lotions or milks usually contain oils or emollients to provide specific tactile properties. These oils are usually added at concentrations between 1 wt. % and 20 wt. % and can derive from extraction processes of natural raw materials such as sunflower oil, avocado oil, sweet almond oil, jojoba oil. Other oils are manufactured from natural or synthetic raw materials via chemical processes. This group includes esters of linear or branched fatty acids with 6-30 carbons with monohydric or polyhydric alcohol containing between 3 and 20 carbons. Non-limiting examples for oils of this group are triglycerides such as caprylic/capric triglyceride, propylene glycol diesters such as propylene glycol dicaprylate/dicaprate, butylene glycol diesters such as butylene glycol dicaprylate/dicaprate, isopropylesters of myristic or palmitic acid. Also included can be hydrocarbons from vegetal or fossil origin such as squalane or mineral oil. Further, esters of aromatic acids such as C12-15 alkylbenzoate may be added in order to improve the solubility of UV filters. Silicons like cyclomethicone of dimethicone are frequently added to cosmetic formulations in order to improve the tactile properties. They may be added for these purposes to a skin care formulation according to the present invention.

Moisturizers are used to improve the skin humidity after application of a cosmetic product. Suitable systems have the intrinsic capacity to transport water into the skin and therefore need to contain hydrophilic groups in their molecule. As examples moisturizers might be chosen from the group of polyols such as glycerol or glycols such as propylene glycol, butylene glycol, pentylene glycol, 1,2-hexanediol or hexylene glycol. The antimicrobial effect which some of these components may contribute is specifically noted and appreciated in this respect.

Viscosity regulators are added to increase or reduce the viscosity of a cosmetic formulation. Suitable thickeners can be chosen from the same group mentioned above for the hair treatment products, viscosity reducing agents can be chosen from the group of medium chain glycols such as Caprylyl glycol or 1,2-decandiol or from the group of glycerine ethers such as ethylhexyl glycerine. The antimicrobial effect which some of these components may contribute is specifically noted and appreciated in this respect.

Refattying agents help to retain or deliver oil components to the skin. Non-limiting examples from the group of refattying components are monoglycerides of medium chain fatty acids like glyceryl caprylate, glyceryl caprate or glyceryl laurate which may be added to formulations according to the present invention. The antimicrobial effect which some of these components may contribute is specifically noted and appreciated in this respect.

Pigments may be added for decorative purposes or to reflect irradiation. As an example they may be chosen from the group of iron oxides, titanium oxide, zinc oxide, silica or carmine.

UV filters may be added to the cosmetic formulation in order to protect the skin from the harmful effect of UV irradiation.

Antioxidants may be added to the cosmetic formulation in order to protect it against rancidity or to capture radicals in the skin which could lead to premature aging of the same. Suitable antioxidants may be chosen from the group of natural and synthetic tocopherols or tocopheryl esters, ascorbyl palmitate, polyphenols and flavonoids extracted from green tea.

Solubilizers: Solubilizers help to incorporated insoluble components into transparent formulations. They are mainly composed of a small lipophilic part and a larger hydrophilic part in the molecule and can derive from addition reaction of ethylene oxide to fatty acids or fatty alcohols. A suitable representative from this group is PEG-40 hydrogenated castor oil. They also may be manufactured from by esterification from polyols and fatty acids e.g. polyglyceryl-10 Laurate or oligosaccharides and fatty esters or alcohols e.g. Caprylyl Glycoside.

Preserving agents: Preserving agents may be chosen from the same group mentioned above for the hair treatment products.

Method of Manufacturing:

As for products of hair treatment the defined mixtures of the cationic starch polymers can be introduced into manufacturing process of the cosmetic product either as blends or separately. Preferably, they should be added to the aqueous phase. The addition of the cationic starch polymers may be executed at any temperature between room temperature or 80° C. Heat sensitive or volatile ingredients should be added to the formulation at the end at room temperature.

What is claimed is:

1. A cosmetic and/or dermatological composition comprising as an effective amount of a conditioning system:
   a) between 0.01-10.0 wt. % of a linear or branched modified starch polymer of the general formula

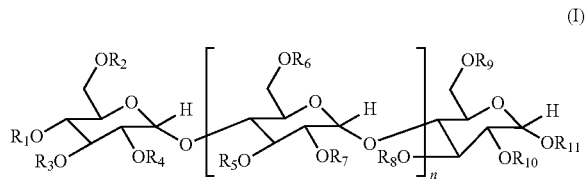

(I)

where $R_1$-$R_{11}$ are independently H or a hydroxyalkyl residue of the general formula —$CH_2$—CHOH—$R_{12}$ with $R_{12}$ being —$CH_3$ or —$CH_2NR_{13}(CH_3)_2{}^+X^-$ with $R_{13}$=—$CH_3$ or a linear or branched $C_4$-$C_{22}$-alkyl residue and with $X^-$=$Cl^-$, $Br^-$ or $I^-$, where n is such that the average molecular weight of the polymer (I) is in the range of 200,000-1,000,000 Da and where the amount of hydroxyl groups carrying a cationic charge is between 25 wt. % and 50 wt. %, which corresponds to a degree of quaternization of D.S.=0.75 and 1.50 and b) between 0.01 and 10.0 wt. % of a linear or branched modified starch polymer of the general formula

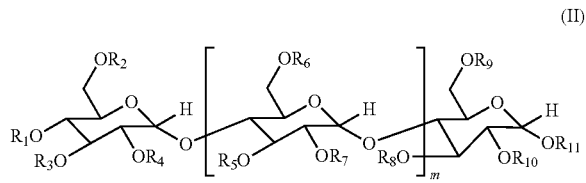

(II)

where $R_1$-$R_{11}$ are independently H or a hydroxyalkyl residue of the general formula —$CH_2$—CHOH—$R_{12}$ with $R_{12}$ formula being —$CH_3$ or —$CH_2NR_{13}(CH_3)_2{}^+X^-$ with $R_{13}$=—$CH_3$ or a linear or branched $C_4$-$C_{22}$-alkyl residue and with $X^-$=$Cl^-$, $Br^-$ or $I^-$, where m is such that the average molecular weight of the polymer (II) is in the range of 2,000,000-8,000,000 Da and where the amount of hydroxyl groups carrying a cationic charge is between 2 wt. % and 20 wt. %, which corresponds to a degree of quaternization of D.S.=0.06 and 0.60 in a cosmetic acceptable medium.

2. The cosmetic and/or dermatological composition according to claim 1 containing an antimicrobially effective amount of a masking agent from the group of p-anisic acid and/or levulinic acid.

3. The cosmetic and/or dermatological composition according to claim 1 containing an antimicrobially effective amount of a re-fattying agent and/or humectant from the group of polyols of the general structure $CH_3(CH_2)_x CHOHCH_2OH$ with x=2-7, and/or a glycerylmonoester of fatty acids with 8-12 carbons.

4. The cosmetic and/or dermatological composition according to claim 1 containing an antimicrobially effective amount of a co-surfactant from the group of lactylates of fatty acids with 8-12 carbons.

5. The cosmetic and/or dermatological composition according to claim 1 in which the total amount of modified starch polymer is between 0.05 and 2.0 wt. % as conditioners.

6. The cosmetic and/or dermatological composition according to claim 5 in which the ratio of the modified starch polymers a) and b) is between 5:1 and 1:5.

7. The cosmetic and/or dermatological composition according to claim 6 containing as antimicrobially effective masking agent p-anisic acid and/or levulinic acid in concentrations between 0.0005 and 0.5 wt. % each.

8. The cosmetic and/or dermatological composition according to claim 6 containing as antimicrobially effective re-fattying agent and/or humectant one or more polyols of the general structure $CH_3(CH_2)_x CHOHCH_2OH$ with x=2-7 or a glycerylmonoester of fatty acids with 8-12 carbons in concentrations between 0.002 and 2 wt. %.

9. The cosmetic and/or dermatological composition according to claim 6, containing as antimicrobially effective co-surfactant one or more lactylates of fatty acids with 8-12 carbons in concentrations between 0.002 and 2 wt. %.

10. A method for treating keratin containing substrates which comprises applying to said substrate a cosmetic and/or dermatological composition according to claim 1.

11. The method of claim 10 wherein the keratin containing substrate comprises hair or skin.

* * * * *